(12) United States Patent
Hamied et al.

(10) Patent No.: US 6,348,458 B1
(45) Date of Patent: Feb. 19, 2002

(54) POLYMORPHIC FORMS OF OLANZAPINE

(75) Inventors: Yusuf K. Hamied; Rajendra N. Kankan, both of Mumbai; Dharmaraj R. Rao, Thane, all of (IN)

(73) Assignee: U & I Pharmaceuticals Ltd., Long Island, NY (US)

( * ) Notice: Subject to any disclaimer, the term of this patent is extended or adjusted under 35 U.S.C. 154(b) by 0 days.

(21) Appl. No.: 09/540,749

(22) Filed: Mar. 31, 2000

(30) Foreign Application Priority Data

Dec. 28, 1999 (IN) ........................ 977/BOM/99
Dec. 28, 1999 (IN) ........................ 972/BOM/99

(51) Int. Cl.[7] ..................... A61K 31/55; C07D 243/06; A61P 25/00; A61P 1/00
(52) U.S. Cl. ........................ 514/220; 540/557
(58) Field of Search ...................... 514/220; 540/557

(56) References Cited

U.S. PATENT DOCUMENTS

| | | | |
|---|---|---|---|
| 4,115,568 A | 9/1978 | Chakrabarti et al. | 424/250 |
| 4,115,574 A | 9/1978 | Chakrabarti et al. | 424/250 |
| 5,229,382 A | 7/1993 | Chakrabarti et al. | 514/220 |
| 5,457,101 A | 10/1995 | Greenwood et al. | 514/220 |
| 5,605,897 A | 2/1997 | Beasley, Jr. et al. | 514/220 |
| 5,627,178 A | 5/1997 | Chakrabarti et al. | 514/220 |
| 5,631,250 A | 5/1997 | Bunnell et al. | 514/220 |
| 5,637,584 A | 6/1997 | Larsen | 514/220 |
| 5,696,115 A | * 12/1997 | Rasmussen | 514/220 |
| 5,703,232 A | 12/1997 | Bunnell et al. | 540/557 |
| 5,736,541 A | 4/1998 | Bunnell et al. | 514/220 |
| 5,817,655 A | 10/1998 | Chakrabarti et al. | 514/220 |
| 5,817,656 A | 10/1998 | Beasley, Jr. et al. | 514/220 |
| 5,817,657 A | 10/1998 | Beasley, Jr. et al. | 514/220 |
| 5,919,485 A | 7/1999 | Cochran et al. | 424/480 |

OTHER PUBLICATIONS

Schmitt et al., Targeting Nicotinic Acetylcholine Receptors: Advances in Molecular Design and Therapies, Annual Reports in Medicinal Chemistry, vol. 35, pp. 41–51, 2000.*

Chakrabarti, et al., 10–Piperazinyl–4H–thieno[3,2–b][1–5] –and –[3,4–b][1,5]benzodiazepines as Potential Neuroleptics, J. Med. Chem. 1980, vol. 23, 884–889.

Chakrabarti, et al., Effects of conformationally Restricted 4–Piperazinyl–10H–thienobenzodiazepine Neuroleptics on Central Dopaminergic and Cholinergic Systems, J. Med. Chem., 1982, vol. 25, pp. 1133–1140.

Drugs of the Future, *Olanzapine*, 1994, vol. 19(2), pp. 114–117.

Chakrabarti et al., 4–Piperazinyl–10H–thieno[2,3–b][1,5] benzodiazepines as Potential Neuroleptics, J. Med. Chem, 1980, vol. 23, pp. 878–884.

* cited by examiner

Primary Examiner—Brenda Coleman
(74) Attorney, Agent, or Firm—Venable; Keith G. Haddaway; Julie Petruzzelli

(57) ABSTRACT

The invention provides three new polymorphic forms of 2-methyl-4-[4-methyl-1-piperazinyl]-10H-thieno[2,3b][1,5] benzodiazepine (Olanzapine) (Formula A), the process for preparing the new polymorphs and pharmaceutical compositions containing the polymorphs. The new polymorphic forms of olanzapine are useful for the treatment of psychotic conditions, mild anxiety and gastrointestinal conditions.

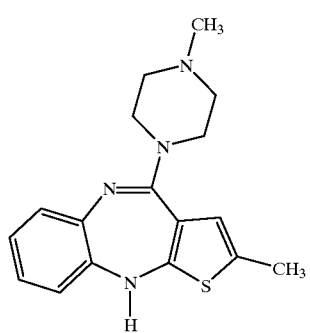

A

42 Claims, 6 Drawing Sheets

POLYMORPHIC FORMS OF OLANZAPINE

BACKGROUND OF THE INVENTION

1. Field of the Invention

This invention relates to novel forms of 2-methyl-4-(4-methyl-1-piperazinyl)-10H-thieno-[2,3b][1,5] benzodiazepine (Formula A) also known as olanzapine. More specifically, the invention provides novel forms of solvate free olanzapine, methods for preparing the novel forms of olanzapine and pharmaceutical formulations containing the novel forms of olanzapine.

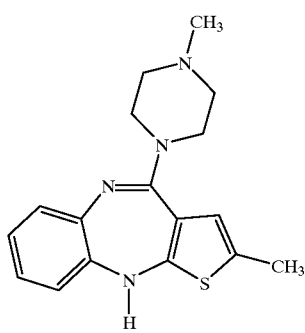

A

2. Background

As described in U.S. Pat. No. 5,736,541 (hereinafter "the '541 patent"), the synthesis of olanzapine according to the methods described in U.S. Pat. No. 5,229,382 produces a metastable, dull colored product referred to in the '541 patent as "Form I." The '541 patent is herein incorporated by reference in its entirety. The '541 patent discloses and claims a more stable polymorphic form of olanzapine, designated as "Form II", a method to produce "Form II" olanzapine, and pharmaceutical compositions containing "Form II" olanzapine. "Form I" and "Form II" olanzapine are characterized in the '541 patent by powder X-ray diffraction. The interplanar spacings (d-spacings) and typical relative intensities (I/I₁) are reported.

U.S. Pat. No. 5,703,232 (hereinafter "the '232 patent") claims lower alcohol solvates of olanzapine referred to in the '232 patent as "Form I" and methods for their preparation. The polymorph designated as "Form I" in the '232 patent has the same characteristic interplanar spacing by X-ray diffraction as "Form II" of the '541 patent and should thus be considered the same polymorph. Similarly, the polymorph designated as "Form II" in the '232 patent has the same characteristic interplanar spacing by X-ray diffraction as the polymorph designated as "Form I" in the '541 patent and should thus be considered the same polymorph. As used hereinafter the terms "Form I" and "Form II" refer to the olanzapine products designated as "Form I" and "Form II" in the '541 patent having the interplanar spacings and typical relative intensities shown in Table 1.

The present invention satisfies a need for additional stable, anhydrous and solvate-free polymorphic forms of olanzapine useful in the preparation of pharmaceutical formulations.

SUMMARY OF THE INVENTION

The present invention provides new polymorphic forms of 2-methyl-4-[4-methyl-1-piperazinyl]-10H-thieno[2,3b][1,5] benzodiazepine (olanzapine) designated as "Form III", "Form IV" and "Form V", methods of preparing the new polymorphic forms of olanzapine and pharmaceutical compositions containing them.

The invention produces new substantially pure polymorphs of olanzapine in high yield. The invention further differs from the prior art by requiring only aqueous solvents to prepare the stable polymorphs. The invention also provides an advantage over the prior art by isolating the new olanzapine polymorphs in a solvent free media, thus producing olanzapine free of solvates and having a negligible solvent content.

The invention provides three novel, solvate free forms of olanzapine designated Form III, Form IV and Form V. The novel forms of olanzapine are characterized by their unique x-ray diffraction patterns and infrared spectra.

The invention further provides a process for preparing the novel forms of olanzapine by first dissolving olanzapine in an aqueous organic or inorganic acid, which may be acetic acid, formic acid, hydrochloric acid, sulfuric acid, citric acid, fumaric acid or maleic acid; and is preferably hydrochloric acid, sulfuric acid, formic acid or acetic acid. The new form of olanzapine is then precipitated using an aqueous or alcoholic solution of alkali, which may be potassium hydroxide, sodium hydroxide or ammonia. The alcoholic solvent may be any mono, di, or polyhydric alcohol, preferably methanol. The olanzapines obtained typically contain less than 5% of other forms of olanzapine and less than 1% of other impurities. The desired form of olanzapine can be obtained by varying the acid or its concentration, and the temperature and pH of precipitation. The acid solution used in preparing the novel forms of olanzapine may contain between about 5% and about 50% acid. Olanzapine is preferably precipitated at a temperature between about 0° C. and about 100° C., more preferably between about 0° C. and about 35° C. and most preferably between about 10° C. and about 30° C. The final pH of the solution, after precipitation, is preferably between about 6 and about 12, and more preferably between about 8 and about 11.

The invention also provides pharmaceutical formulations containing as an active ingredient at least one of the novel forms of olanzapine according to the invention or a pharmaceutically acceptable salt thereof. The invention further provides a method of treating a psychotic condition, mild anxiety or gastrointestinal conditions by administering an effective amount of at least one of Form III, Form IV or Form V olanzapine or a pharmaceutically acceptable salt thereof to a patient.

The above objectives and advantages of the invention are illustrative, and not exhaustive, of those which can be achieved by the invention and the examples presented herein are non-limiting. Thus, these and other objectives and advantages of the invention will be apparent from the description herein, both as embodied herein and as modified in view of any variations which will be apparent to those skilled in the art.

BRIEF DESCRIPTION OF THE DRAWINGS

Embodiments of the invention are explained in greater detail by way of the accompanying figures.

DETAILED DESCRIPTION OF THE INVENTION

The process of the present invention consists of dissolving olanzapine in aqueous acid and precipitating olanzapine from the resultant salt solution using an aqueous or alcoholic solution of alkali. Alcoholic solutions include any mono-, di- or polyhydric alcohol. A methanolic solution is particularly preferred. The acids to be used in the present invention may be any suitable organic or inorganic acid, for example, hydrochloric acid, sulfuric acid, acetic acid, formic acid, citric acid, fumaric acid, and maleic acid. Preferred acids are hydrochloric acid, sulfuric acid, acetic acid and formic acid. The concentration of acid may range from 5% to 50%.

Either Form I or Form II olanzapine may be used as a starting material in the invention. The preferred olanzapine used in preparing the novel polymorphs of the invention is Form I olanzapine obtained by the method described in U.S. Pat. No. 5,229,382, which is herein incorporated by reference in its entirety.

The Form I or Form II olanzapine is mixed with the selected acid and stirred at a suitable temperature until dissolved completely. The solution is then neutralized using a base selected from aqueous or alcoholic sodium hydroxide, aqueous or alcoholic potassium hydroxide or aqueous ammonia. The alcohol solvent may be any mono, di, or polyhydric alcohol. Methanol is a preferred alcoholic solvent.

The temperature of precipitation is preferably between about 0° C. and about 100° C., more preferably between about 0° C. and about 35° C. and most preferably between about 10° C. and about 30° C. During precipitation, the pH of the precipitate is preferably adjusted to be between about 6 and about 12, and more preferably between about 8 and about 11. The novel polymorphs of the invention are obtained in substantially pure form. The term "substantially pure" as used herein means that the polymorphs contain less than 5% of other forms of olanzapine and less than 1% of other impurities, water or solvates.

Figure 3:
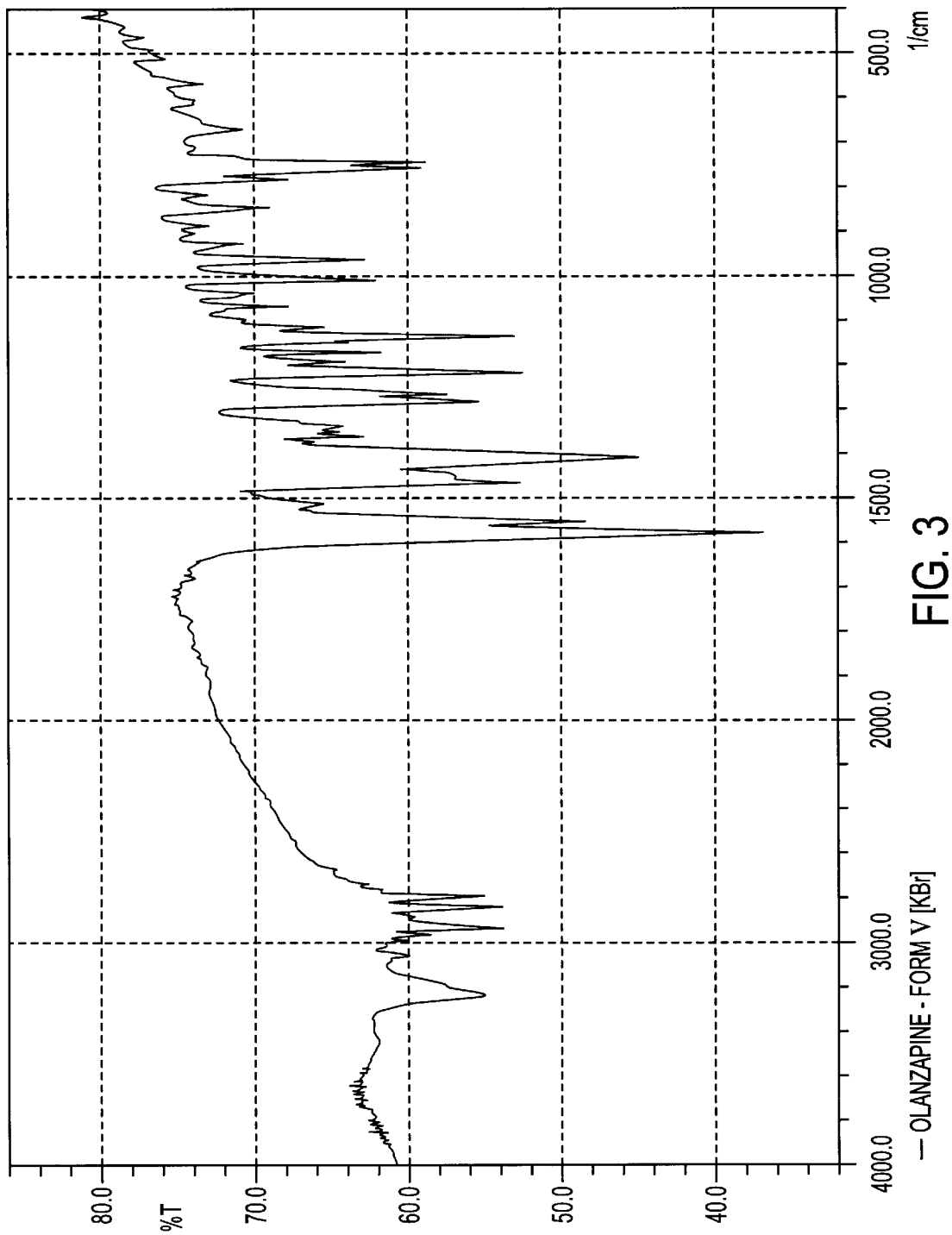
FIG. 3 is a FT-IR spectrum of Form V olanzapine.
Figure 4:
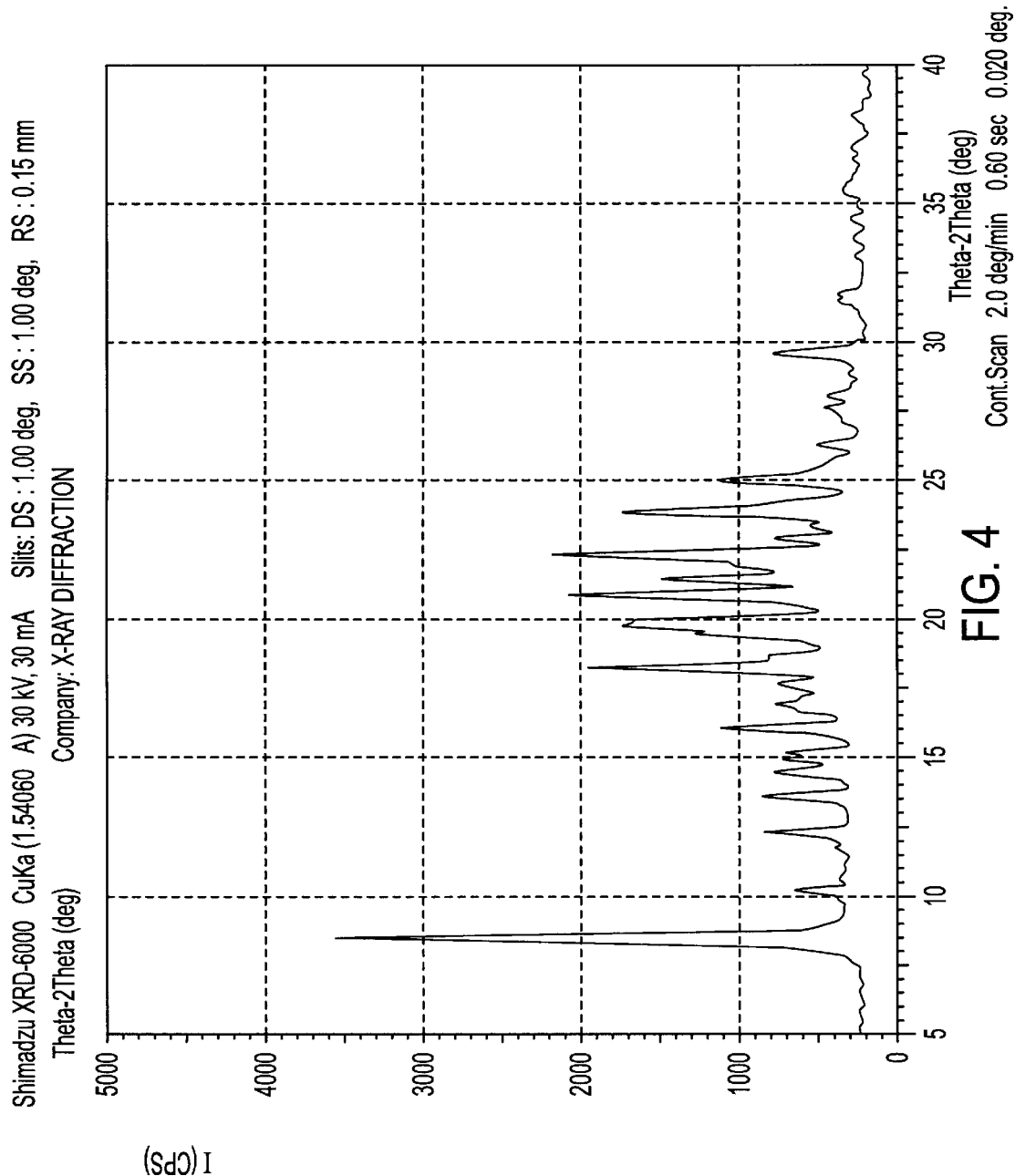
FIG. 4 is the X-ray diffraction pattern obtained for Form III olanzapine.
Figure 5:
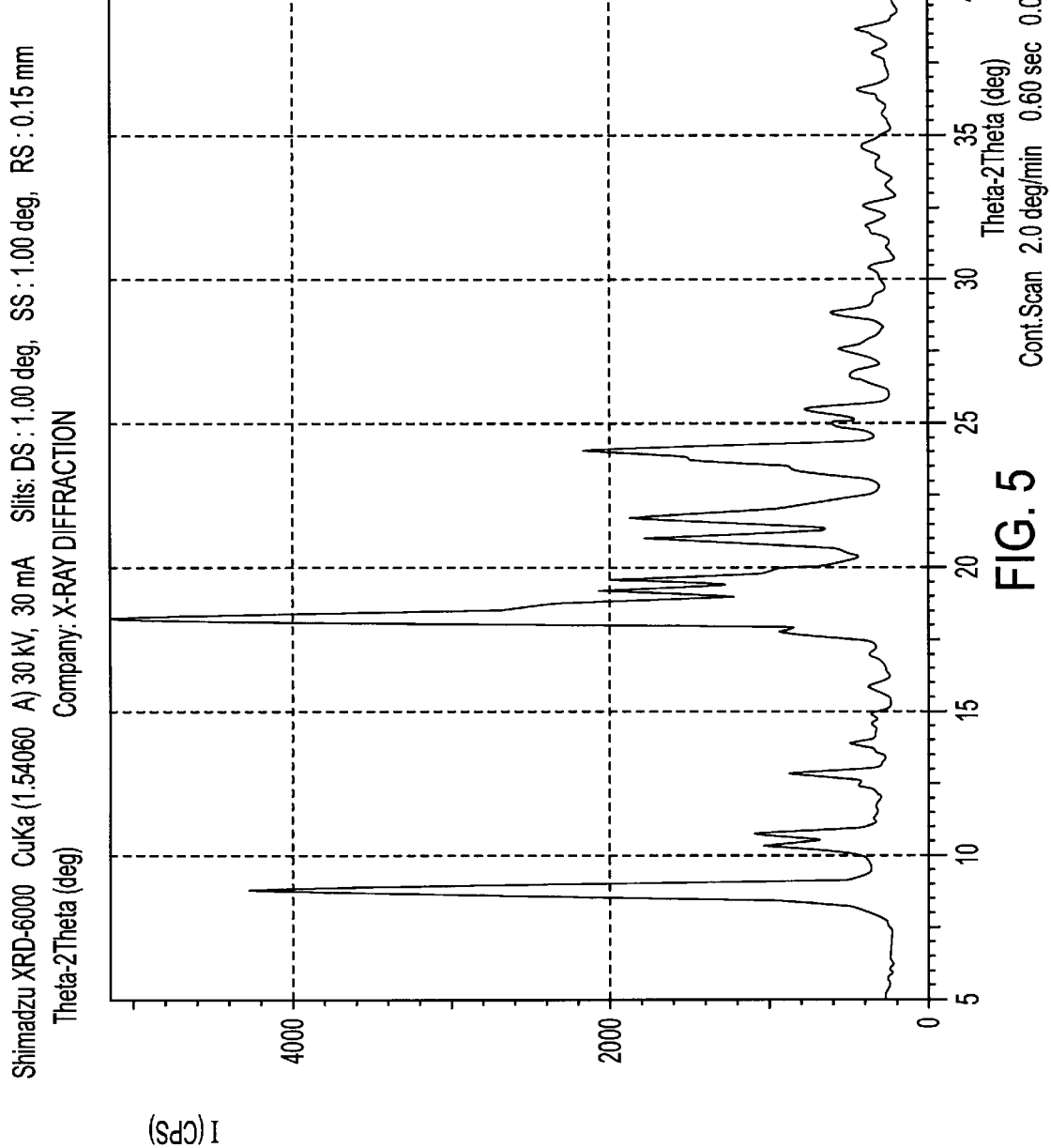
FIG. 5 is the X-ray diffraction pattern obtained for Form IV olanzapine.
Figure 6:
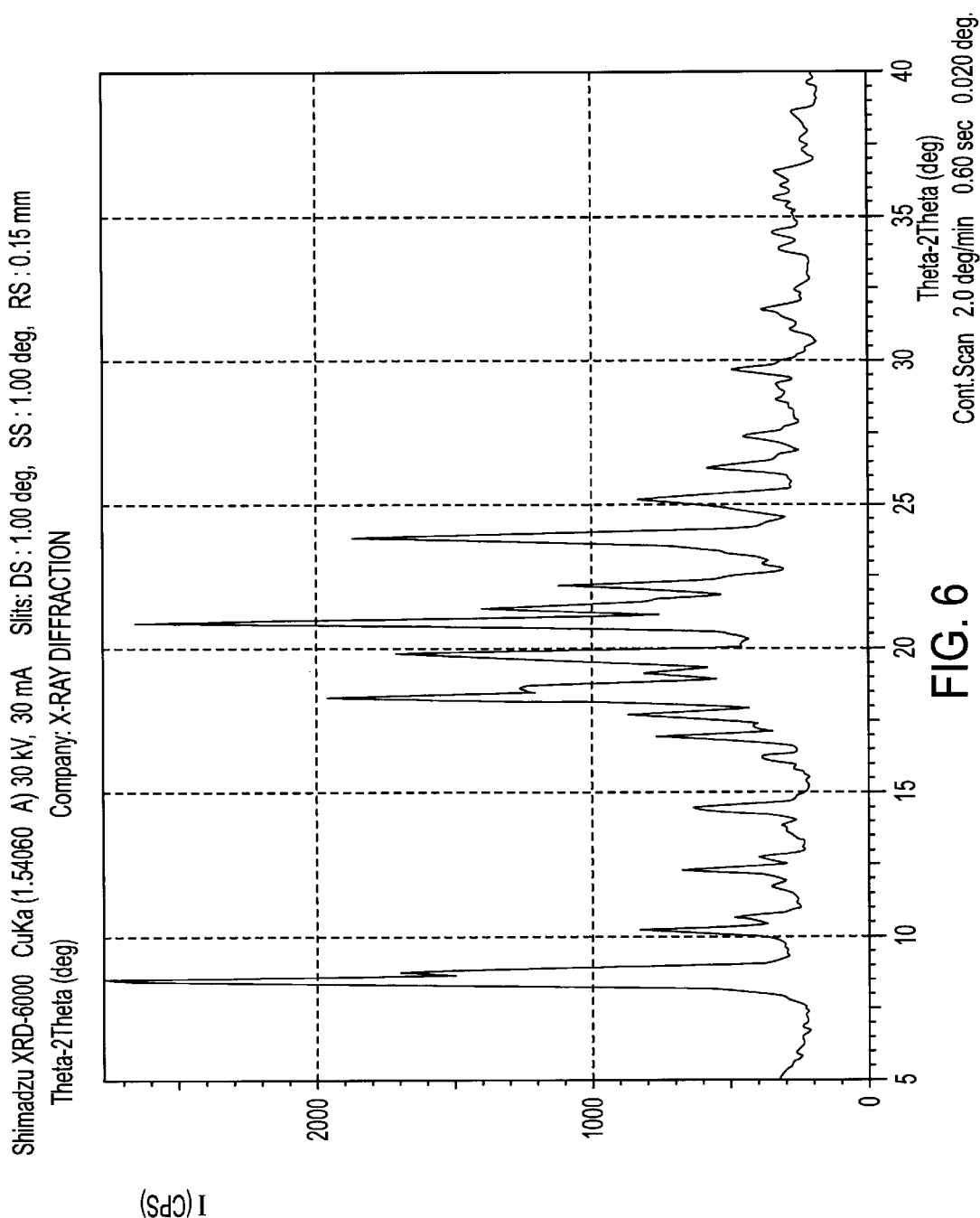
FIG. 6 is the X-ray diffraction pattern obtained for Form V olanzapine.

The novel polymorphs of the invention have been characterized by powder x-ray diffraction (XRD) patterns obtained using a Shimadzu X-ray diffractometer XRD-6000, equipped with a wide range goniometer and using copper K$\alpha$ radiation as set forth in FIGS. 4–6. The interplanar spacings (in Angstrom and typical relative intensities (I/I$_1$) sufficient to identify Forms III, IV, and V olanzapine according to the invention are set forth in Table 3. The complete set of interplanar spacings and relative intensities for Forms III, IV, and V olanzapine are set forth in Table 5. The novel polymorphs were further characterized by infrared (IR) spectroscopy obtained in a KBr disk using a Shimadzu FT-IR 8201 PC system as set forth in FIGS. 1–3. The IR absorbances (in wavenumbers, cm$^{-1}$) sufficient to identify Forms III, IV, and V olanzapine are set forth in Table 2. The complete set of IR absorbances for Forms III, IV, and V olanzapine are set forth in Table 4.

Form III olanzapine may be prepared by dissolving Form I or Form II olanzapine in about 50% aqueous acetic acid and precipitating the compound using about 15% aqueous ammonia to a final pH of about 8. Alternatively, Form III olanzapine may be obtained by dissolving Form I or Form II olanzapine in about 33% aqueous acetic acid and precipitating the compound using about 50% aqueous sodium hydroxide to a pH of about 10. Form III olanzapine is characterized by the infrared (IR) spectrum of FIG. 1 and by the X-ray diffraction pattern (XRD) of FIG. 4. The IR absorbances and XRD peaks sufficient to identify Form III olanzapine are contained in Tables 2 and 3, respectively. The complete set of IR absorbances and XRD peaks for Form III olanzapine are provided in Tables 4 and 5, respectively.

Form IV olanzapine may be prepared by dissolving Form I or Form II olanzapine in about 38% aqueous formic acid and precipitating the compound using about 10% methanolic sodium hydroxide to a final pH of about 8. Alternatively, Form IV olanzapine may be prepared by dissolving Form I or Form II olanzapine in about 43% aqueous acetic acid and precipitating the compound using about 25% ammonia to a final pH of about 10. Form IV olanzapine is characterized by the IR spectrum of FIG. 2 and by the XRD of FIG. 5. The IR absorbances and XRD peaks sufficient to identify Form IV olanzapine are contained in Tables 2 and 3, respectively. The complete set of IR absorbances and XRD peaks for Form IV olanzapine are provided in Tables 4 and 5, respectively.

Form V olanzapine may be prepared by dissolving Form I or Form II olanzapine in about 10% aqueous hydrochloric acid and precipitating the compound using about 10% aqueous sodium hydroxide to a final pH of about 8.5. Alternatively, Form V olanzapine may be prepared by dissolving Form I or Form II olanzapine in about 40% aqueous acetic acid and precipitating the compound using about 50% aqueous sodium hydroxide to a final pH of about 9. Form V olanzapine may also be obtained by dissolving Form I or Form II olanzapine in about 20% formic acid and precipitating the compound using about 25% aqueous ammonia. Also, Form V olanzapine may be prepared by dissolving Form I or Form II olanzapine in about 50% acetic acid and precipitating the compound using about 25% ammonia to a final pH of about 9. Form V olanzapine is characterized by the IR spectrum of FIG. 3 and by the XRD of FIG. 6. The IR absorbances and XRD peaks sufficient to identify Form V olanzapine are contained in Tables 2 and 3, respectively. The complete set of IR absorbances and XRD peaks for Form V olanzapine are provided in Tables 4 and 5, respectively.

The methods of the invention may be used for the purification of olanzapine, as well as for preparation of the new polymorphic forms. For example, 97% pure (by HPLC) Form I olanzapine may be converted to approximately 99% pure Form III olanzapine (HPLC) by dissolving olanzapine in about 33% aqueous acetic acid and precipitating Form III olanzapine using about 50% aqueous sodium hydroxide to a final pH of about 10.

Olanzapine has been found to have a wide range of therapeutic effects, particularly for the treatment of schizophrenia, schizophreniform disorders, psychosis, mild anxiety states and functional bowel disorders. The various disorders which may be treated using olanzapine are described in detail in the '541 patent at column 4, line 62 through column 8, line 55.

Pharmaceutical formulations according to the invention comprise Form III, IV or V olanzapine or a pharmaceutically acceptable salt thereof as an active ingredient together with one or more pharmaceutically acceptable carriers, excipients or diluents. Any conventional technique may be used for the preparation of pharmaceutical formulations according to the invention. Examples of suitable carriers include sugars, starches, gum acacia, calcium phosphate, alginates, tragacanth, gelatin, syrup, methyl cellulose, methyl- and propyl-hydroxy-benzoate, talc, magnesium stearate or mineral oil. The active ingredient may be contained in a formulation that provides quick release, sustained release or delayed release after administration to the patient.

Pharmaceutical compositions may be formulated for transdermal delivery, oral delivery or as a suppository. Formulations may be in the form of capsules, tablets or gels for oral delivery or as a suspension for transermal delivery. Pharmaceutical compositions according to the present invention may preferably contain 0.25 to 100 mg of active ingredient or, more prefereably, 1 to 30 mg active ingredient, along with a pharmaceutically acceptable carrier.

Methods

Figure 1:
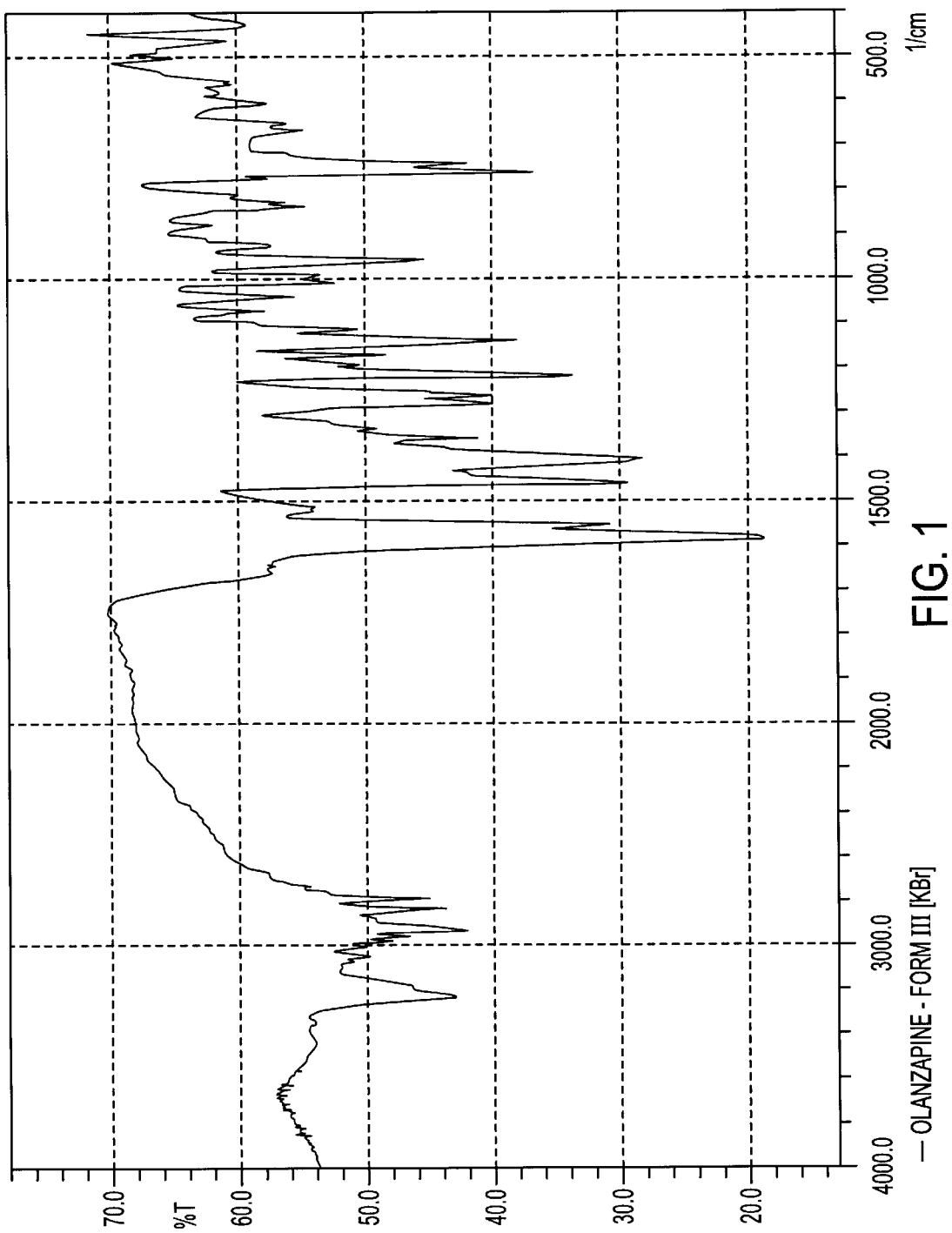
FIG. 1 is a FT-IR spectrum of Form III olanzapine.
Figure 2:
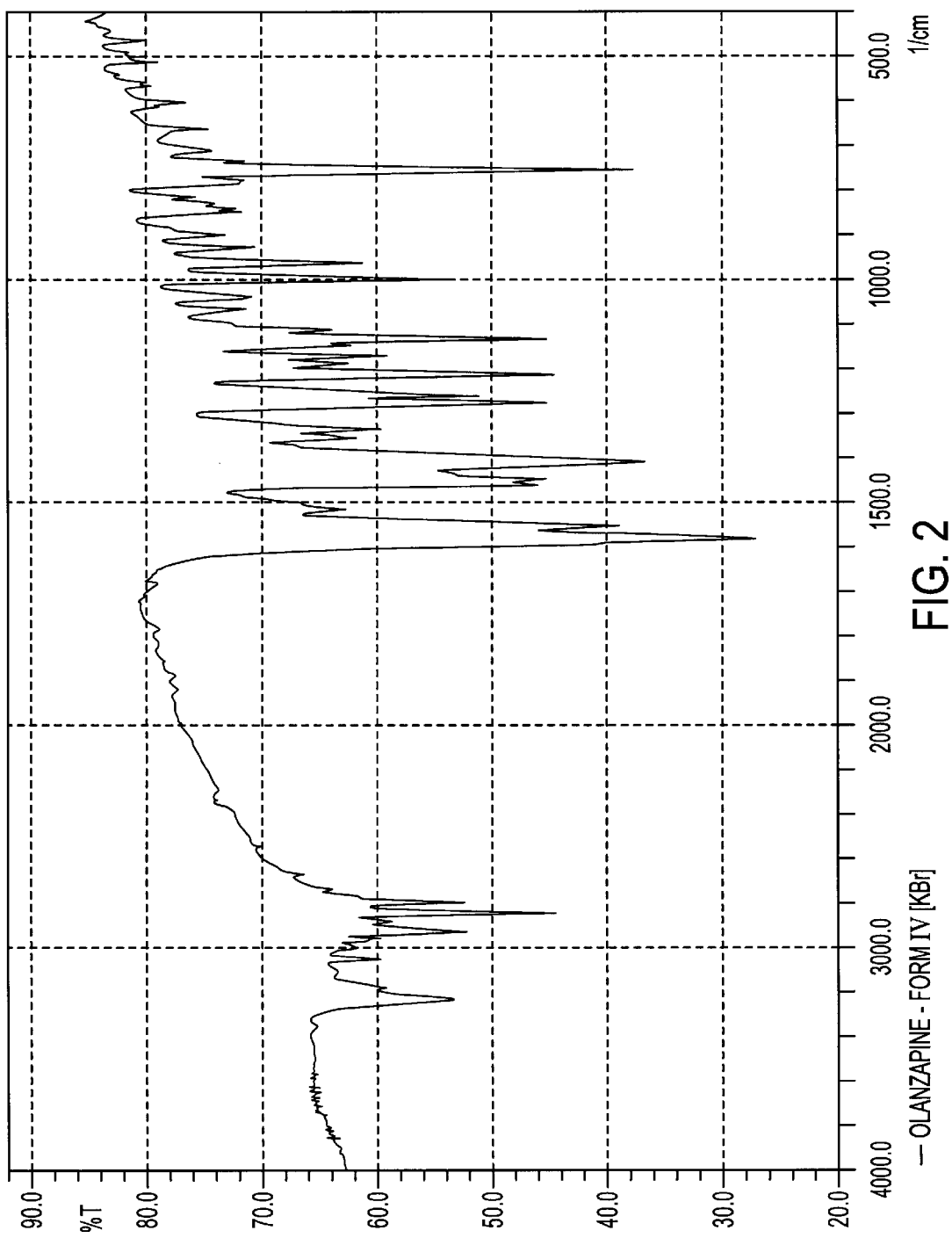
FIG. 2 is a FT-IR spectrum of Form IV olanzapine.

Form I olanzapine used as a starting material was obtained by the method described in U.S. Pat. No. 5,229,382. IR-Spectra were obtained in a KBr disk using a Shimadzu FT-IR 8201 PC system. The IR-Spectra obtained for the three polymorphic forms, i.e. Forms III, IV, and V, are shown in FIGS. 1, 2 and 3, respectively. A summary of wavenumbers sufficient to identify Forms III, IV and V olanzapine is provided in Table 2. Table 4 contains a complete listing of IR absorbances for Forms III, IV and V olanzapine according to the invention. Powder x-ray diffraction patterns were obtained on a Shimadzu X-ray diffractometer XRD-6000, equipped with a wide range goniometer using copper K$\alpha$ radiation. The powder x-ray diffraction patterns for the three polymorphic forms, i.e. Forms III, IV, and V, are provided in FIGS. 4, 5 and 6, respectively. The interplanar d-spacings sufficient to identify Forms III, IV and V olanzapine and their relative intensities are set forth in Table 3. The complete set of interplanar d-spacings and relative intensities for Forms III, IV and V olanzapine are provided in Table 5.

EXAMPLE 1

Form I olanzapine (10 g) was dissolved in a mixture of 30 ml acetic acid and 30 ml water by stirring. Activated charcoal (0.5 g) was added and the contents filtered over celite. The clear solution was maintained at 20° C. and 15% aqueous ammonia solution was added over a period of 30 minutes to adjust the pH to 8. The contents were filtered and dried to obtain Form III olanzapine (9.6 g), which was characterized by IR and XRD.

EXAMPLE 2

Form I olanzapine (10 g) was dissolved in a mixture of 30 ml acetic acid and 40 ml water and the contents filtered over celite. The clear solution was maintained at 20° C. and 30 ml of 25% aqueous ammonia solution was added rapidly in 10 minutes to adjust the pH to about 6. The solids precipitated slowly and the solution was stirred for 30 minutes. A further 30 ml of ammonia solution was added to the mass to obtain a pH of about 10. The contents were further stirred for 1 hour and filtered and dried to obtain Form IV olanzapine (9.4 g), which was charcterized by IR and XRD.

EXAMPLE 3

Form I olanzapine (10 g) was disolved in a mixture of 40 ml acetic acid and 60 ml water and the contents filtered over celite. The clear solution was maintained at 20° C. and 50 ml of 50% aqueous sodium hydroxide solution was added rapidly with stirring to obtain a gummy mass. On stirring for a further 30 minutes, a fine suspension was obtained. The pH of the contents was adjusted to about 9 using additional sodium hydroxide solution. The product was recovered by filtration and dried to obain Form V olanzapine (9.4 g), which was characterized by IR and XRD.

EXAMPLE 4

Form I olanzapine (10 g) was dissolved in a mixture of 25 ml formic acid and 40 ml water by stirring. Activated charcoal (0.5 g) was added and the contents were filtered over celite. The clear solution was maintained at 10 to 15° C. and neutralized with 10% methanolic sodium hydroxide solution to a pH of 8. The product was recovered by filtration and dried to obtain Form IV olanzapine (9.3 g), which was characterized by IR and XRD.

EXAMPLE 5

Form I olanzapine (10 g) was dissolved in a mixture of 10 ml formic acid and 40 ml water and the solution was filtered over celite. This solution was added slowly to a stirred 25% aqueous ammonia solution (70 ml) to which a few seed crystals of Form V olanzapine were added. The temperature was maintained between 15 to 25° C. during the addition. The contents were stirred for 1 hour and filtered and dried to obtain Form V olanzapine (9.4 g), which was characterized by IR and XRD.

EXAMPLE 6

Form I olanzapine (10 g) obtained by the method described in U.S. Pat. No. 5,229,352 and having a purity of 97% (HPLC) was dissolved in a mixture of 30 ml acetic acid and 60 ml water and the solution filtered over celite. The solution was maintained at 20° C. with stirring and 50% aqueous sodium hydroxide solution added to adjust the pH to between 6 and 6.2. The solids which precipitated were stirred for 45 minutes and filtered. The wet cake was taken up in water (50 ml) and additional sodium hydroxide added to adjust the pH to 10. The contents were stirred for 1 hour and filtered. The product was dried to obtain >99% pure Form III olanzapine (9.1 g), which was characterized by IR and XRD.

EXAMPLE 7

Form I olanzapine (10 g) was dissolved in 50 ml of 10% hydrochloric acid with stirring. Activated charcoal (0.5 g)

was added and the contents filtered over celite. The clear solution was maintained at 15° C. and neutralized to a pH of 8.5 with 10% aqueous sodium hydroxide solution. The product was recovered by filtration and dried to obtain Form V olanzapine (9.5 g), which was characterized by IR and XRD.

EXAMPLE 8

Form I olanzapine (10 g) was dissolved in a mixture of 30 ml acetic acid and 30 ml water and the contents filtered over celite. This solution was added to 60 ml of a stirred 25% aqueous ammonia solution seeded with a few crystals of Form V olanzapine. The temperature was maintained at 15 to 25° C. during the addition of the Form I solution to the aqueous ammonia solution and the pH of the mass was 9 after completion of the addition. After stirring for 1 hour, the product was recovered by filtration and dried to obtain Form V olanzapine which was characterized by IR and XRD.

Certain representative embodiments of the invention are described in the examples given above. The materials used and the process steps are intended as illustrative of the invention and the invention is not limited to the methods, process steps or any other conditions described in the examples. The examples are non-limiting and may be modified or varied, and elements added or omitted, without departing from the invention, as appreciated by those skilled in the art.

TABLE - 1

X-RAY DIFFRACTION PEAKS OF FORM I AND FORM II OLANZAPINE SUMMARY OF d-spacing AND $I/I_1$ INTENSITY RATIO

| FORM I | | FORM II | |
|---|---|---|---|
| d-spacing | $I/I_1$ | d-spacing | $I/I_1$ |
| 9.9463 | 100.00 | 10.2689 | 100.00 |
| 8.5579 | 15.18 | 8.577 | 7.96 |
| 8.2445 | 1.96 | 7.4721 | 1.41 |
| 6.8862 | 14.73 | 7.125 | 6.50 |
| 6.3787 | 4.25 | 6.1459 | 3.12 |
| 6.2439 | 5.21 | 6.071 | 5.12 |
| 5.5895 | 1.10 | 5.4849 | 0.52 |
| 5.3055 | 0.95 | 5.2181 | 6.86 |
| 4.9815 | 6.14 | 5.1251 | 2.47 |
| 4.8333 | 68.37 | 4.9874 | 7.41 |
| 4.7255 | 21.88 | 4.7665 | 4.03 |
| 4.6286 | 3.82 | 4.7158 | 6.80 |
| 4.533 | 17.83 | 4.4787 | 14.72 |
| 4.4624 | 5.02 | 4.3307 | 1.48 |
| 4.2915 | 9.19 | 4.2294 | 23.19 |
| 4.2346 | 18.88 | 4.141 | 11.28 |
| 4.0855 | 17.29 | 3.9873 | 9.01 |
| 3.8254 | 6.49 | 3.7206 | 14.04 |
| 3.7489 | 10.64 | 3.5645 | 2.27 |
| 3.6983 | 14.65 | 3.5366 | 4.85 |
| 3.5817 | 3.04 | 3.3828 | 3.47 |
| 3.5064 | 9.23 | 3.2516 | 1.25 |
| 3.3392 | 4.67 | 3.134 | 0.81 |
| 3.2806 | 1.96 | 3.0848 | 0.45 |
| 3.2138 | 2.52 | 3.0638 | 1.34 |
| 3.1118 | 4.81 | 3.0111 | 3.51 |
| 3.0507 | 1.96 | 2.8739 | 0.79 |
| 2.948 | 2.40 | 2.8102 | 1.47 |
| 2.8172 | 2.89 | 2.7217 | 0.20 |
| 2.7589 | 2.27 | 2.6432 | 1.26 |
| 2.6597 | 1.86 | 2.6007 | 0.77 |
| 2.6336 | 1.10 | | |
| 2.5956 | 1.73 | | |

TABLE - 2

FT-IR PEAKS OF FORM III, FORM IV AND FORM V OLANZAPINE SUMMARY OF WAVENUMBERS

| FORM-III $cm^{-1}$ | FORM-IV $cm^{-1}$ | FORM-V $cm^{-1}$ |
|---|---|---|
| — | 604 | 604 |
| 611 | — | — |
| 656 | 661 | — |
| 671 | — | 671 |
| 746 | — | 746 |
| 765 | 758 | 758 |
| 845 | — | 847 |
| — | 904 | — |
| 935 | 931 | 928 |
| — | — | 1357 |
| 1369 | 1365 | 1369 |
| — | 1456 | — |

TABLE - 3

X-RAY DIFFRACTION PEAKS OF FORM III, FORM IV AND FORM V OLANZAPINE SUMMARY OF d-spacing AND $I/I_1$ INTENSITY RATIO

| FORM-III | | | FORM-IV | | | FORM-V | | |
|---|---|---|---|---|---|---|---|---|
| 2-theta [deg.] | d-spacing | $I/I_1$ | 2-theta [deg.] | d-spacing | $I/I_1$ | 2-theta [deg.] | d-spacing | $I/I_1$ |
| 8.5649 | 10.3156 | 100 | 8.8814 | 9.9487 | 83 | 8.3400 | 10.5932 | 17 |
| 12.3325 | 7.1713 | 16 | 10.3898 | 8.5074 | 15 | 8.6477 | 10.2170 | 100 |
| 13.6091 | 6.5014 | 17 | 10.7669 | 8.2103 | 17 | 8.8800 | 9.9503 | 57 |

TABLE - 3-continued

X-RAY DIFFRACTION PEAKS OF FORM III, FORM IV AND FORM V OLANZAPINE SUMMARY OF d-spacing AND I/I₁ INTENSITY RATIO

| FORM-III | | | FORM-IV | | | FORM-V | | |
|---|---|---|---|---|---|---|---|---|
| 2-theta [deg.] | d-spacing | I/I₁ | 2-theta [deg.] | d-spacing | I/I₁ | 2-theta [deg.] | d-spacing | I/I₁ |
| 16.0535 | 5.5165 | 24 | 18.4029 | 4.8172 | 100 | 10.3673 | 8.5259 | 22 |
| 18.2617 | 4.8541 | 46 | 18.8200 | 4.7114 | 41 | 12.4540 | 7.1016 | 17 |
| 19.4600 | 4.5578 | 24 | 19.2284 | 4.6122 | 35 | 14.5737 | 6.0731 | 17 |
| 19.7400 | 4.4938 | 38 | 19.5884 | 4.5282 | 33 | 17.0243 | 5.2041 | 19 |
| 19.9200 | 4.4536 | 36 | 20.9646 | 4.2340 | 29 | 17.7763 | 4.9856 | 20 |
| 20.8409 | 4.2588 | 49 | 21.7109 | 4.0901 | 32 | 18.4102 | 4.8153 | 62 |
| 22.2635 | 3.9898 | 52 | 23.6600 | 3.7574 | 23 | 18.6600 | 4.7514 | 34 |
| 23.8442 | 3.7288 | 42 | 24.0400 | 3.6989 | 40 | 19.5800 | 4.5302 | 24 |
| 24.9738 | 3.5626 | 25 | | | | 19.8400 | 4.4714 | 51 |
| 29.4932 | 3.0262 | 18 | | | | 20.9993 | 4.2271 | 91 |
| | | | | | | 21.4949 | 4.1307 | 40 |
| | | | | | | 22.2738 | 3.9880 | 31 |
| | | | | | | 23.5400 | 3.7763 | 10 |
| | | | | | | 23.9232 | 3.7167 | 62 |
| | | | | | | 25.1975 | 3.5315 | 22 |

TABLE - 4

COMPLETE FT-IR PEAKS OF FORM III, FORM IV AND FORM V OLANZAPINE SUMMARY OF WAVENUMBERS

| FORM-III cm⁻¹ | FORM-IV cm⁻¹ | FORM-V cm⁻¹ |
|---|---|---|
| — | 604 | 604 |
| 611 | — | — |
| 656 | 661 | — |
| 671 | — | 671 |
| 746 | — | 746 |
| 765 | 758 | 758 |
| 845 | — | 847 |
| — | 904 | — |
| 935 | 931 | 928 |
| 966 | 970 | 966 |
| 1008 | 1005 | 1006 |
| 1348 | 1344 | 1344 |
| — | — | 1357 |
| 1369 | 1365 | 1369 |
| 1414 | 1419 | 1414 |
| — | 1456 | 1414 |
| — | 1456 | — |
| 1469 | 1469 | 1469 |
| 1560 | 1560 | 1560 |
| 1593 | 1589 | 1585 |
| 2790 | 2798 | 2792 |
| 2837 | 2842 | 2839 |
| 2933 | 2927 | 2931 |
| 3232 | 3234 | 3228 |

TABLE - 5

COMPLETE X-RAY DIFFRACTION PEAKS OF FORM III, FORM IV AND FORM V OLANZAPINE SUMMARY OF d-spacing AND I/I₁ INTENSITY RATIO

| FORM-III | | | FORM-IV | | | FORM-V | | |
|---|---|---|---|---|---|---|---|---|
| 2-theta [deg.] | d-spacing | I/I₁ | 2-theta [deg.] | d-spacing | I/I₁ | 2-theta [deg.] | d-spacing | I/I₁ |
| 8.22 | 10.7476 | 15 | 8.88 | 9.9487 | 83 | 8.34 | 10.5932 | 17 |
| 8.56 | 10.3156 | 100 | 10.39 | 8.5074 | 15 | 8.65 | 10.2170 | 100 |
| 10.25 | 8.6245 | 11 | 10.77 | 8.2103 | 17 | 8.88 | 9.9503 | 57 |
| 12.33 | 7.1713 | 16 | 12.88 | 6.8673 | 12 | 10.37 | 8.5259 | 22 |
| 13.61 | 6.5014 | 17 | 17.82 | 4.9734 | 12 | 12.45 | 7.1016 | 17 |
| 14.48 | 6.1120 | 14 | 18.40 | 4.8172 | 100 | 14.57 | 6.0731 | 17 |
| 14.94 | 5.9251 | 12 | 18.82 | 4.7114 | 41 | 17.02 | 5.2041 | 19 |
| 15.20 | 5.8243 | 12 | 19.23 | 4.6122 | 35 | 17.78 | 4.9856 | 20 |
| 16.05 | 5.5165 | 24 | 19.59 | 4.5282 | 33 | 18.41 | 4.8153 | 62 |
| 16.92 | 5.2359 | 11 | 20.96 | 4.2340 | 29 | 18.66 | 4.7514 | 34 |
| 18.26 | 4.8541 | 46 | 21.71 | 4.0901 | 32 | 19.22 | 4.6139 | 15 |
| 18.66 | 4.7514 | 10 | 23.66 | 3.7574 | 23 | 19.58 | 4.5302 | 24 |
| 19.46 | 4.5578 | 24 | 24.04 | 3.6989 | 40 | 19.84 | 4.4714 | 51 |
| 19.74 | 4.4938 | 38 | 25.39 | 3.5052 | 11 | 20.99 | 4.2271 | 91 |
| 19.92 | 4.4536 | 36 | | | | 21.49 | 4.1307 | 40 |

TABLE - 5-continued

COMPLETE X-RAY DIFFRACTION PEAKS OF FORM III, FORM IV AND
FORM V OLANZAPINE SUMMARY OF d-spacing AND I/I₁ INTENSITY RATIO

| FORM-III | | | FORM-IV | | | FORM-V | | |
|---|---|---|---|---|---|---|---|---|
| 2-theta [deg.] | d-spacing | I/I₁ | 2-theta [deg.] | d-spacing | I/I₁ | 2-theta [deg.] | d-spacing | I/I₁ |
| 20.84 | 4.2588 | 49 | | | | 21.80 | 4.0736 | 15 |
| 21.38 | 4.1523 | 30 | | | | 22.27 | 3.9880 | 31 |
| 21.82 | 4.0699 | 15 | | | | 23.54 | 3.7763 | 10 |
| 22.26 | 3.9898 | 52 | | | | 23.92 | 3.7167 | 62 |
| 22.81 | 3.8955 | 10 | | | | 25.20 | 3.5315 | 22 |
| 23.84 | 3.7288 | 42 | | | | 26.38 | 3.3762 | 13 |
| 24.97 | 3.5626 | 25 | | | | 29.70 | 3.0060 | 11 |
| 29.49 | 3.0262 | 18 | | | | | | |

What is claimed is:

1. A process for producing a polymorph of olanzapine comprising:

dissolving an initial polymorph of olanzapine in aqueous acidic solution; wherein the aqueous acidic solution comprises an acid selected from the group consisting of organic and inorganic acids; and precipitating a different polymorph of olanzapine by neutralization; wherein neutralization is accomplished by the addition of an aqueous or alcoholic solution of a base.

2. The process according to claim 1, wherein the acid is selected from the group consisting of hydrochloric acid, sulfuric acid, acetic acid, formic acid, citric acid, fumaric acid and maleic acid.

3. The process according to claim 1, wherein the acid is selected from the group consisting of hydrochloric acid, sulfuric acid, acetic acid and formic acid.

4. The process according to claim 1, wherein the solution of the base is selected from the group consisting of aqueous sodium hydroxide, alcoholic sodium hydroxide, aqueous potassium hydroxide, alcoholic potassium hydroxide and aqueous ammonia.

5. The process according to claim 1, wherein the alcoholic solution of the base comprises an alcohol selected from a mono, di, or polyhydric alcohol.

6. The process according to claim 5, wherein the alcohol is methanol.

7. The process according to claim 1, further comprising the step of:

recovering said different polymorph of olanzapine containing less than 5% of the initial form of olanzapine and less than 1% of other impurities.

8. The process according to claim 1, wherein the initial polymorph of olanzapine is Form I or Form II olanzapine, wherein Form I olanzapine is an olanzapine polymorph having a typical x-ray powder diffraction pattern represented by the following interplanar spacings:

| d-spacings (Å) |
|---|
| 9.9463 |
| 8.5579 |
| 8.2445 |

-continued

| d-spacings (Å) |
|---|
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |

-continued

| d-spacings (Å) |
| --- |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

9. The process according to claim 1, wherein the different polymorph of olanzapine is Form III olanzapine having a typical x-ray powder diffraction pattern comprising the following interplanar spacings:

| d-spacing (Å) |
| --- |
| 10.3156 |
| 7.1713 |
| 6.5014 |
| 5.5165 |
| 4.8541 |
| 4.5578 |
| 4.4938 |
| 4.4536 |
| 4.2588 |
| 3.9898 |
| 3.7288 |
| 3.5626 |
| 3.0262. |

10. The process according to claim 1, wherein the different polymorph of olanzapine is Form IV olanzapine having a typical x-ray powder diffraction pattern comprising the following interplanar spacings:

| d-spacings (Å) |
| --- |
| 9.9487 |
| 8.5074 |
| 8.2103 |
| 4.8172 |
| 4.7114 |
| 4.6122 |
| 4.5282 |
| 4.2340 |
| 4.0901 |
| 3.7574 |
| 3.6989. |

11. The process according to claim 1, wherein the different polymorph of olanzapine is Form V olanzapine having a typical x-ray powder diffraction pattern comprising the following interplanar spacings:

| d-spacing (Å) |
| --- |
| 10.5932 |
| 10.2170 |
| 9.9503 |
| 8.5259 |
| 7.1016 |
| 6.0731 |
| 5.2041 |
| 4.9856 |
| 4.8153 |
| 4.7514 |
| 4.5302 |
| 4.4714 |
| 4.2271 |
| 4.1307 |
| 3.9880 |
| 3.7763 |
| 3.7167 |
| 3.5315. |

12. The process according to claim 1, wherein the precipitation is conducted at a temperature between about 0° C. and about 100° C.

13. The process according to claim 1, wherein the precipitation is conducted at a temperature between about 0° C. and about 35° C.

14. The process according to claim 1, wherein the precipitation is conducted at a temperature between about 10° C. and about 30° C.

15. The process according to claim 1, wherein the precipitation comprises adjusting the pH to between about 6 and about 12.

16. The process according to claim 1, wherein the precipitation comprises adjusting the pH to between about 8 and about 11.

17. The process according to claim 1, wherein the acidic solution comprises from about 5% to about 50% acid.

18. The process according to claim 1, wherein the acidic solution is about 50% acetic acid and the basic solution is about 15% aqueous ammonia.

19. The process according to claim 1, wherein the acidic solution is about 38% formic acid and the basic solution is about 10% methanolic sodium hydroxide.

20. The process according to claim 1, wherein the acidic solution is about 10% hydrochloric acid and the basic solution is about 10% aqueous sodium hydroxide.

21. The process according to claim 1, wherein the acidic solution is about 43% acetic acid and the basic solution is about 25% aqueous ammonia.

22. The process according to claim 1, wherein the acidic solution is about 40% acetic acid and the basic solution is about 50% aqueous sodium hydroxide.

23. The process according to claim 1, wherein the acidic solution is about 20% formic acid and the basic solution is about 25% aqueous ammonia.

24. The process according to claim 1, wherein the acidic solution is about 33% acetic acid and the basic solution is about 50% aqueous ammonia.

25. The process according to claim 1, wherein the acidic solution is about 50% acetic acid and the basic solution is about 25% aqueous ammonia.

26. Form III olanzapine polymorph having a typical x-ray powder diffraction pattern comprising the following interplanar spacings:

| d-spacing (Å) |
| --- |
| 10.3156 |
| 7.1713 |
| 6.5014 |
| 5.5165 |
| 4.8541 |
| 4.5578 |
| 4.4938 |
| 4.4536 |
| 4.2588 |
| 4.0699 |
| 3.9898 |
| 3.7288 |
| 3.5626 |
| 3.0262. |

27. The Form III olanzapine polymorph according to claim 26, further comprising the following x-ray powder diffraction pattern, wherein d represents the interplanar spacing and $I/I_1$ represents the typical relative intensities:

| d-spacing (Å) | $I/I_1$ |
| --- | --- |
| 10.3156 | 100 |
| 7.1713 | 16 |
| 6.5014 | 17 |
| 5.5165 | 24 |
| 4.8541 | 46 |
| 4.5578 | 24 |
| 4.4938 | 38 |
| 4.4536 | 36 |
| 4.2588 | 49 |
| 3.9898 | 52 |
| 3.7288 | 42 |
| 3.5626 | 25 |
| 3.0262 | 18. |

28. The Form III olanzapine polymorph according to claim 26, further characterized by having an infrared spectrum comprising absorbances at the following wavenumbers:

611

656

671

746

765

845

935

1369.

29. The Form III olanzapine polymorph according to claim 26, produced by the process of:

dissolving Form I or Form II olanzapine in 50% aqueous acetic acid, and precipitating substantially pure Form III olanzapine with 15% aqueous ammonia;

wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

30. The Form III olanzapine polymorph according to claim 26, produced by the process of:
   dissolving Form I or Form II olanzapine in about 33% aqueous acetic acid, and
   precipitating substantially pure Form III olanzapine with about 50% aqueous ammonia;
wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |

| d-spacings (Å) |
| --- |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

31. Form IV olanzapine polymorph having a typical x-ray powder diffraction pattern comprising the following interplanar spacings:

| d-spacing (Å) |
| --- |
| 9.9487 |
| 8.5074 |
| 8.2103 |
| 4.8172 |
| 4.7114 |
| 4.6122 |
| 4.5282 |
| 4.2340 |
| 4.0901 |
| 3.7574 |
| 3.6989. |

32. The Form IV olanzapine polymorph according to claim 31, further comprising the following x-ray powder diffraction pattern, wherein d represents the interplanar spacing and $I/I_1$ represents the typical relative intensities:

| d-spacing (Å) | $I/I_1$ |
| --- | --- |
| 9.9487 | 83 |
| 8.5074 | 15 |
| 8.2103 | 17 |
| 4.8172 | 100 |
| 4.7114 | 41 |
| 4.6122 | 35 |
| 4.5282 | 33 |
| 4.2340 | 29 |
| 4.0901 | 32 |
| 3.7574 | 23 |
| 3.6989 | 40. |

33. The Form IV olanzapine polymorph according to claim 31, further characterized by having an infrared spectrum comprising absorbances at the following wavenumbers:
   604
   661
   758
   904
   931
   1365
   1456.

34. The Form IV olanzapine polymorph according to claim 31, produced by the process of:
   dissolving Form I or Form II olanzapine in about 38% aqueous formic acid, and
   precipitating substantially pure Form IV olanzapine using about 10% methanolic sodium hydroxide;

wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |

-continued

| d-spacings (Å) |
| --- |
| 2.6432 |
| 2.6007. |

35. The Form IV olanzapine polymorph according to claim 31, produced by the process of:
   dissolving Form I or Form II olanzapine in about 43% aqueous acetic acid, and
   precipitating substantially pure Form IV olanzapine using about 25% aqueous ammonia;
wherein Form I olanzapine is an olanzapine polymorph having a typical x-ray diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |

-continued

| d-spacings (Å) |
| --- |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

36. Form V olanzapine polymorph having a typical x-ray powder diffraction pattern comprising the following interplanar spacings:

| d-spacing (Å) |
| --- |
| 10.5932 |
| 10.2170 |
| 9.9503 |
| 8.5259 |
| 7.1016 |
| 6.0731 |
| 5.2041 |
| 4.9856 |
| 4.8153 |
| 4.7514 |
| 4.5302 |
| 4.4714 |
| 4.2271 |
| 4.1307 |
| 3.9880 |
| 3.7763 |
| 3.7167 |
| 3.5315. |

37. The Form V olanzapine polymorph according to claim 36, further comprising the following x-ray powder diffraction pattern, wherein d represents the interplanar spacing and I/I$_1$ represents the typical relative intensities:

| d-spacing (Å) | I/I$_1$ |
| --- | --- |
| 10.5932 | 17 |
| 10.2170 | 100 |
| 9.9503 | 57 |
| 8.5259 | 22 |
| 7.1016 | 17 |
| 6.0731 | 17 |
| 5.2041 | 19 |
| 4.9856 | 20 |
| 4.8153 | 62 |
| 4.7514 | 34 |
| 4.5302 | 24 |
| 4.4714 | 51 |
| 4.2271 | 91 |
| 4.1307 | 40 |
| 3.9880 | 31 |
| 3.7763 | 10 |

-continued

| d-spacing (Å) | I/I$_1$ |
| --- | --- |
| 3.7167 | 62 |
| 3.5315 | 22. |

38. The Form V olanzapine polymorph according to claim 36, further characterized by having an infrared spectrum comprising absorbances at the following wavenumbers:

604

671

746

758

847

928

1357

1369.

39. The Form V olanzapine polymorph according to claim 36, produced by the process of:

dissolving Form I or Form II olanzapine in about 10% aqueous hydrochloric acid, and precipitating substantially pure Form V olanzapine using about 10% aqueous sodium hydroxide;

wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

40. The Form V olanzapine polymorph according to claim 36, produced by the process of:

dissolving Form I or Form II olanzapine in about 40% acetic acid, and precipitating substantially pure Form V olanzapine using about 50% aqueous sodium hydroxide;

wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |

-continued

| d-spacings (Å) |
| --- |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
| --- |
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

41. The Form V olanzapine polymorph according to claim 36, produced by the process of:

dissolving Form I or Form II olanzapine in about 20% aqueous formic acid, and precipitating substantially pure Form V olanzapine using about 25% aqueous ammonia;

wherein Form I olanzapine is an olanzapine polymorph having a typical x-ray powder diffraction pattern represented by the following interplanar spacings:

| d-spacings (Å) |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |

-continued

| d-spacings (Å) |
|---|
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

42. The Form V olanzapine polymorph according to claim 36, produced by the process of:
dissolving Form I or Form II olanzapine in about 50% aqueous acid, and
precipitating substantially pure Form V olanzapine using about 25% aqueous ammonia;
wherein Form I olanzapine is an olanzapine polymorph having a typical x-ray powder diffraction pattern represented by the following interplanar spacings:

| d-spacings (Å) |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956; | and Form II olanzapine is an olanzapine polymorph having a typical x-ray powder diffraction pattern represented by the following interplanar spacings:

| d-spacings (Å) |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

\* \* \* \* \*